United States Patent

Dugger, III

[11] Patent Number: 6,110,486
[45] Date of Patent: Aug. 29, 2000

[54] BUCCAL POLAR SPRAY OR CAPSULE

[75] Inventor: Harry A. Dugger, III, Flemington, N.J.

[73] Assignee: Flemington Pharmaceuticals Co., Flemington, N.J.

[21] Appl. No.: 09/199,380

[22] Filed: Nov. 25, 1998

Related U.S. Application Data

[63] Continuation-in-part of application No. 08/630,065, Apr. 12, 1996, abandoned.
[51] Int. Cl.⁷ ..................................................... A61F 13/02
[52] U.S. Cl. ........................................... 424/435; 424/434
[58] Field of Search ..................................... 424/435, 434

[56] References Cited

U.S. PATENT DOCUMENTS 4,232,002  11/1980  Nogrady ..................................... 424/45

FOREIGN PATENT DOCUMENTS

3922650A1   1/1990   Germany .

Primary Examiner—Carlos A. Azpuru
Attorney, Agent, or Firm—Omri M. Behr, Esq.

[57] ABSTRACT

A buccal aerosol spray or capsule using a polar solvent has now been developed which provides biologically active compounds for rapid absorption through the oral mucosa, resulting in fast onset of effect. The buccal aerosol spray of the invention comprises: polar solvent 5–50%, active compound 1–40%, flavoring agent 0.05–5%. The soft bite gelatin capsule of the invention comprises as comprising as fill composition: polar solvent 75–99%, emulsifier 0–20%, active compound 0.03–35%, and flavoring agent 0.05–60%.

9 Claims, 1 Drawing Sheet

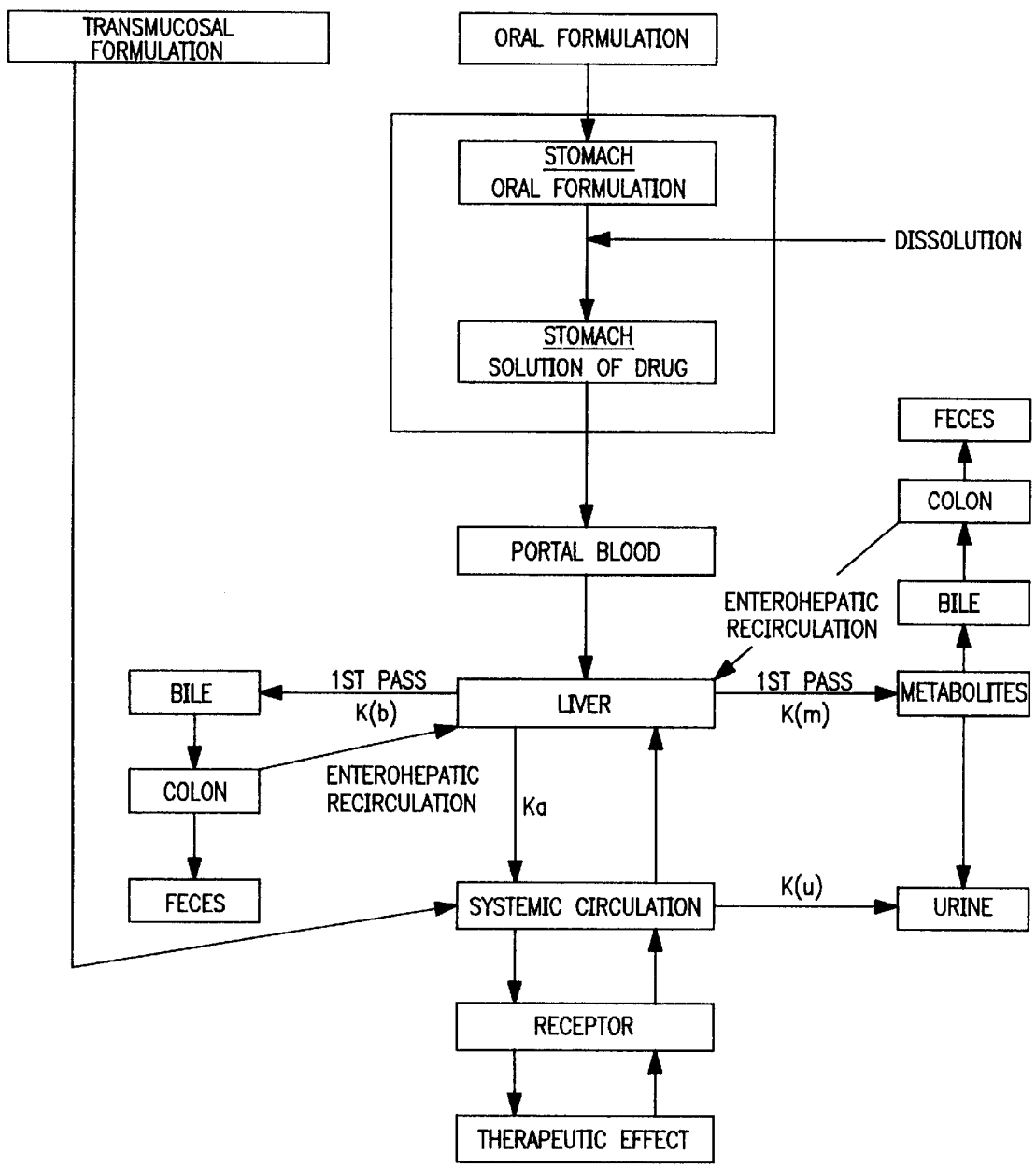

BUCCAL POLAR SPRAY OR CAPSULE

RELATED APPLICATIONS

This application is a continuation-in-part of application Ser. No. 08/630,065, filed Apr. 12, 1996 now abandoned.

BACKGROUND OF THE INVENTION

It is known that certain biologically active compounds are better absorbed through the oral mucosa than through other routes of administration, such as through the stomach or intestine. However, formulations suitable for such administration by these latter routes present their own problems. For example, the biologically active compound must be compatible with the other components of the composition such as propellants, solvents, etc. Many such formulations have been proposed. For example, U.S. Pat. No. 4,689,233, Dvorsky et al., describes a soft gelatin capsule for the administration of the anti-coronary drug nifedipine dissolved in a mixture of polyether alcohols. U.S. Pat. No. 4,755,389, Jones et al., describes a hard gelatin chewable capsule containing nifedipine. A chewable gelatin capsule containing a solution or dispersion of a drug is described in U.S. Pat. No. 4,935,243, Borkan et al. U.S. Pat. No. 4,919,919, Aouda et al, and U.S. Pat. No. 5,370,862, Klokkers-Bethke, describe a nitroglycerin spray for administration to the oral mucosa comprising nitroglycerin, ethanol, and other components. An orally administered pump spray is described by Cholcha in U.S. Pat. No. 5,186,925. Aerosol compositions containing a hydrocarbon propellant and a drug for administration to a mucosal surface are described in U.K. 2,082,457, Su, U.S. Pat. No. 3,155,574, Silson et al., U.S. Pat. No. 5,011,678, Wang et al., and by Parnell in U.S. Pat. No. 5,128,132. It should be noted that these references discuss bioavailability of solutions by inhalation rather than through the membranes to which they are administered. The former requiring the use of far lower concentrations of active material than for the latter.

SUMMARY OF THE INVENTION

A buccal spray or soft bite gelatin capsule using a polar solvent has now been developed which provides biologically active com-pounds for rapid absorption through the oral mucosa, resulting in fast onset of effect.

The oral mucosal delivery using a spray was overlooked in the past, (1) because it was thought that the time available for absorption was very short because of the natural cleaning of the mouth by swallowing the saliva, and (2) it was thought that in the time available one could not have absorption of the total dose. As a result, most, if not all formulations under development for transmucosal transfer target the nose which is thought to have a longer residence time or use sustained release mechanisms such as patches, suckers, buccal tablets, etc. Using the formulation in the present application, the time available is longer than previously expected, in that it has been found that up to 30 minutes was available for the absorption phase, before clearance of the mouth reduced the concentration of the drug in the mouth thus slowing the absorption process.

Further, it has been found that while it is true that the total dose cannot be delivered to the blood through the oral mucosa in the time available, one does not have to deliver the entire dose through the mucosal membranes to achieve the fast onset. The fraction need to achieve therapeutic blood levels is only a small part of the total dose. This is in part due to by-passing the first pass effect of the liver and in part due to the delivery of the absorption of the drug from a solution directly into the blood, instead from the stomach-intestines using a tablet, which must first undergo dissolution before absorption can take place (FIG. 1).

The buccal spray compositions of the present invention, for transmucosal administration of a pharmacologically active compound soluble in a pharmacologically acceptable polar solvent comprising in weight % of total composition: polar solvent 75–99.8%, active compound 1–20%, suitably additionally comprising, by weight of total composition a flavoring agent 0.05–5%. Preferably the composition comprises: polar solvent 75–99%, active compound 1–20%, flavoring agent 0.1–2.5%; most suitably polar solvent 75–98%, active compound 1–12.5%, flavoring agent 0.1–2.5%.

The soft bite gelatin capsules of the present invention for transmucosal administration of a pharmacologically active compound, at least partially soluble in a pharmacologically acceptable polar solvent, having charged thereto a composition comprising in weight % of total composition: polar solvent 40–99.8%, emulsifier 0–20%, active compound 0.03–35%, provided that said composition contains less than 10% of water, suitably additionally comprising, by weight of the composition: flavoring agent 0.05–60%. Preferably, the soft bite gelatin capsule still comprises: polar solvent 50–99.8%, emulsifier 0–15%, active compound 0.03–26%, flavoring agent 0.5–55%; most suitably: polar solvent 70–99.5%, emulsifier 0–10%, active compound 0.15–24.0%, flavoring agent 0.1–50%. It is particularly desirable to formulate the gelatin portion of the capsule with a softening agent such as glycerine, sodium lauryl sulfate or the like to improve chewability and shelf life.

It is an object of the invention to coat the mucosal membranes either with extremely fine droplets of spray without the use of a propellant other than slightly compressed atmospheric air containing the active compounds, or a solution or paste thereof from bite capsules.

The spray compositions of the invention are intended to be administered from a pump spray by means of low level compression of atmospheric air.

It is also an object of the invention to administer to a mammalian need of same preferably man, a predetermined amount of a biologically active compound by this method or from a soft gelatin bite capsule.

A further object is a pump spray container containing a composition of the spray formulation, and a metered valve suitable for releasing from said container a predetermined amount of said composition.

The solvent is a low molecular weight, pharmacologically acceptable alcohol, water, glycerine or polyethylene glycol or mixtures thereof.

A further object is a soft gelatin bite capsule containing a composition as set forth above. The formulation may be in the form of a viscous solution or paste containing the active compounds. Although solutions are preferred, paste fills may also be used where the active compound is not soluble or only partially soluble in the solvent of choice. Where water is used to form part of the solvent or paste composition, it should not exceed 10% thereof. (All percentages herein are by weight unless otherwise indicated.)

The polar solvent is chosen such that it is compatible with the gelatin shell and the active compound. The solvent preferably dissolves the active compound. However, other components wherein the active compound is not soluble or only slightly soluble may be used and will form a paste fill.

Soft gelatin capsules are well known in the art. See, for example, U.S. Pat. No. 4,935,243, Borkan et al., which is incorporated herein by reference for its teaching of such capsules. The capsules of the present invention are intended to be bitten into to release the high viscosity solution or paste therein, which will then coat the buccal mucosa with the active compounds. Typical capsules, which are swallowed whole or bitten and then swallowed, deliver the active compounds the stomach, which results in significant lag time before maximum blood levels can be achieved or subject the compound to a large first pass effect. Because of the enhanced absorption of the compounds through the oral mucosa and no chance of a first pass effect, use of the bite capsules of the invention will eliminate much of the lag time, resulting in hastened onset of biological effect. The shell of a soft gelatin capsule of the invention may comprise, for example: gelatine 50–75%, glycerine 20–30%, colorants 0.5–1.5%, water 5–10%, and sorbitol 2–10%.

BRIEF DESCRIPTION OF THE DRAWING

The FIGURE is a schematic diagram showing routes of absorption and processing of pharmacologically active substances in a mammalian system.

DESCRIPTION OF THE PREFERRED EMBODIMENTS

The preferred active compounds of the present invention are nicotine, clemastine, testosterone, estradiol, progesterone, fluoxetine, and piroxicam in their nonionized form or as the free base of the pharmaceutically acceptable salts thereof (provided, for the spray compositions, they are soluble in the spray solvent). These compounds are soluble in the non-polar solvents of the invention at useful concentrations or can be prepared as pastes at useful concentrations. These concentrations may be less than the standard accepted dose for these compounds since there is enhanced absorption of the compounds through the oral mucosa. This aspect of the invention is especially important when there is a large (40–99.99%) first pass effect.

The spray compositions of the present invention are formulated for oral transmucosal administration rather than delivery to the lung mucosa. Thus, the formulations of the present invention require a concentration level of pharmacological agents of about one order of magnitude (10×) higher than those delivered to the lung.

As solvents for the sprays there may be used low molecular weight polyethyleneglycols (PEG) of 200–1000 MW (preferably 200–600). Low molecular weight alcohols and polyols, such as glycerin may also be present and water may also be used.

Suitable solvents for the capsules include low molecular weight polyethyleneglycols (PEG) of 400–1000 MW (preferably 400–600). Low molecular weight alcohols and polyols, such as glycerin may also be present and water may also be used. However, these should only be used sparingly in the bite capsule compositions as they may migrate into the gelatin shell and weaken it.

It is expected that some glycerin and water used to make the gelatin shell will migrate from the shell to the fill during the curing of the shell. Likewise, there may be some migration of components from the fill to the shell during curing and even throughout the shelf-life of the capsule. Therefore, the values given herein are for the compositions as prepared, it being within the scope of the invention that minor variations will occur.

The preferred flavoring agents are synthetic or natural oil of peppermint, oil of spearmint, citrus oil, fruit flavors, chocolate, sweeteners (sugars, aspartame, saccharin, etc.), and combinations thereof.

The active substances include the active compounds selected from the group consisting of antihistamines, steroid hormones, non-steroidal anti-inflammatories, Anti-depressants and benzo-diazepines, such as tamezepam.

Clemastine hydrogen fumarate is a known (Tavist®, Sandoz) anti-histamine. Both the spray and capsule of the invention advantageously coat the oral mucosa with an immediately available dose of clemastine which can be rapidly absorbed. This is highly desirable, as during an acute asthma attack.

Testosterone is a hormone produced by gonadal cells. Testosterone, especially the esters thereof (e.g., acetate, propionate, enanthate, and cypionate), is used in the treatment of hypogonadism.

Estradiol is an estrogen steroid secreted from the ovaries. Estradiol, especially the esters thereof (e.g., diacetate, and benzoate), is used as estrogen replacement therapy, especially in post-menopausal women.

Progesterone is a hormone produced by the corpus luteum. Fluoxetine is an antidepressant also known as Prozac. Piroxicam is a known (Feldene®, Pfizer) anti-inflammatory.

The formulations of the present invention comprise an active compound or a pharmaceutically acceptable salt thereof. The term "pharmaceutically acceptable salts" refers to salts prepared from pharmaceutically acceptable non-toxic acids or bases including organic and inorganic acids or bases.

When an active compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glutamine, glucosamine, histidine, isopropylamine, lysine, methylglucosamine, morpholine, piperazine, piperidine, polyamine resins, procaine, purine, theobromine, triethylamine, trimethylamine, tripropylamine, etc.

When an active compound of the present invention is basic, salts may be prepared from pharmaceutically acceptable non-toxic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, mandelic, methanesulfonic, mucic, nitric, pamoic, panto-thenic, phosphoric, succinic, sulfuric, tartaric, p-toluenesulfonic, etc. Particularly preferred are citric, hydrobromic, maleic, phosphoric, sulfuric, and tartaric acids.

In the discussion of methods of treatment herein, reference to the active compounds is meant to also include the pharmaceutically acceptable salts thereof. While certain formulations are set forth herein, the actual amounts to be administered to the mammal in need of same are to be determined by the treating physician.

The invention is further defined by reference to the following examples, which are intended to be illustrative and not limiting.

EXAMPLE 1

Clemastine Spray

A spray of the invention comprises the following formulation:

|  | Amount |
| --- | --- |
| Polar solvent: | |
| Ethanol | 66% |
| Water | 31 % |
| Clemastine fumarate | 0.68–2.6% |
| Peppermint Oil | 0.2% |

It is particularly preferred to formulate the spray delivering 1.34 mg/activation.

EXAMPLE 2

Fluoxetine Hydrochloride Spray

A spray of the invention comprises the following formulation:

|  | Preferred Amount | Most-Preferred Amount |
| --- | --- | --- |
| Polar solvent | 75–98% | 75–95% |
| Fluoxetine Hydrochloride | 2.5–20% | 5–12.5% |
| Flavoring agent | 0.1–2.5% | 0.1–2.0% |

It is particularly preferred to formulate the spray delivering 5 mg/activation:

|  | Amount |
| --- | --- |
| Polar solvent: | |
| Ethanol | 48.4% |
| Water | 10.0% |
| Polyethyleneglycol | 30.0% |
| Fluoxetine HCl | 10.6% |
| Oil of Orange | 1.0% |

EXAMPLE 3

Testosterone Spray Delivering 3 mg/Activation

A spray of the invention comprises the following formulation:

|  | Amount | Preferred Amount | Most-Preferred Amount |
| --- | --- | --- | --- |
| Polar Solvent | 55–99% | 75–95% | 85–93% |
| Testosterone | 2–10% | 3–7.5% | 4–6.5% |
| Flavoring Agent | 0.05–3% | 0.1–2.5% | 0.1–2.5% |

It is particularly preferred to formulate the spray:

|  | Amount |
| --- | --- |
| Polar solvent: | |
| Water | 10% |
| Polyethyleneglycol | 65% |
| Ethanol | 16.6% |
| Testosterone | 6.4% |
| Orange Aroma | 1.0% |
| Oil of Citrus | 1.0% |

EXAMPLE 4

Estradiol Spray Delivering 0.1 mg/Activation

A spray of the invention comprises the following formulation:

|  | Amount | Preferred Amount | Most-Preferred Amount |
| --- | --- | --- | --- |
| Polar Solvent | 55–99% | 75–95% | 85–93% |
| Estradiol | 1–2.5% | 1–2.0% | 1.0–1.5% |
| Flavoring Agent | 0.05–3% | 0.1–2.5% | 1–2.0% |

It is particularly preferred to formulate the spray:

|  | Amount |
| --- | --- |
| Polar solvent: | |
| Water | 0.5% |
| Polyethyleneglycol | 85% |
| Ethanol | 9.5% |
| Estradiol | 2.0% |
| Peppermint | 1.0% |

EXAMPLE 5

Progesterone Spray Delivering 0.32 mg/Activation

A spray of the invention comprises the following formulation:

|  | Amount | Preferred Amount | Most-Preferred Amount |
| --- | --- | --- | --- |
| Polar Solvent | 60–90% | 75–85% | 75–80% |
| Progesterone | 1–20% | 1–10% | 1–5% |
| Flavoring Agent | 0.05–5% | 2–5% | 3–5% |

It is particularly preferred to formulate the spray:

|  | Amount |
| --- | --- |
| Polar solvent: | |
| Water | 0.5% |
| Polyethyleneglycol | 75% |
| Ethanol | 9.5% |
| Progesterone | 10% |
| Peppermint | 1.0% |

EXAMPLE 6

Clemastine Bite Capsule

A bite capsule of the invention comprises the following fill formulation:

|  | Amount | Preferred Amount | Most-Preferred Amount |
|---|---|---|---|
| Polar Solvent | 55–99% | 66–97% | 85–99.5% |
| Emulsifier | 0–20% | 0–15% | 0–10% |
| Clemastine fumarate | 0.1–4% | 0.3–3% | 0.4–1.5% |
| Flavoring agent | 0.05–5% | 0.1–2.5% | 0.1–2.5% |

It is particularly preferred to formulate the composition fill for a 1.34 mg capsule:

|  | Amount |
|---|---|
| Polar solvent: |  |
| Polyethyleneglycol | 89.6%% |
| Water | 5.3% |
| Glycerine | 4.4% |
| Clemastine fumarate | 0.50% |
| Peppermint Oil | 0.1% |
| Saccharine | 0.1% |

EXAMPLE 7
Testosterone Bite Capsule

A bite capsule of the invention comprises the following fill formulation:

|  | Amount | Preferred Amount | Most-Preferred Amount |
|---|---|---|---|
| Polar Solvent | 55–99% | 66–97% | 85–99.5% |
| Emulsifier/wetting agents | 0–20% | 0–15% | 0–10% |
| Testosterone* | 0.1–3.7% | 0.4–3% | 0.7–2% |
| Flavoring agent | 0.05–5% | 0.1–2.5% | 0.1–2.5% |

*or esters thereof, preferably, the acetate, propionate, and enenthate esters

It is particularly preferred to formulate the fill composition for the 5 mg capsule:

|  | Amount |
|---|---|
| Polar solvent: |  |
| Polyethyleneglycol | 85.0% |
| Glycerine | 6.15% |
| Lecithin | 6.0% |
| Testosterone | 1.85% |
| Peppermint Oil | 1.0% |

EXAMPLE 8
Estradiol Bite Capsule

A bite capsule of the invention comprises the following fill formulation:

|  | Amount | Preferred Amount | Most-Preferred Amount |
|---|---|---|---|
| Polar Solvent | 75–99% | 75–99.8% | 85–99.5% |
| Emulsifier/wetting agents | 0–20% | 0–15% | 0–10% |
| Estradiol* | 0.03–2% | 0.03–0.75% | 0.02–0.2% |
| Flavoring agent | 0.05–5% | 0.1–2.5% | 0.1–2.5% |

*or esters thereof, preferably, the diacetate and benzoate esters

It is particularly preferred to formulate the fill composition for a 0.5 mg capsule:

|  | Amount |
|---|---|
| Polar solvent: |  |
| Polyethyleneglycol | 85% |
| Glycerine | 8.82% |
| Lecithin | 5.0% |
| Estradiol | 0.18% |
| Oil of Peppermint | 1.0% |

EXAMPLE 9
Progesterone Bite Capsule

A bite capsule of the invention comprises the following fill

|  | Amount | Preferred Amount | Most-Preferred Amount |
|---|---|---|---|
| Polar solvent | 75–99.8% | 75–98.8% | 85–99.5% |
| Emulsifier/wetting agents | 0–20% | 0–15% | 0–10% |
| Progesterone | 0.3–4% | 0.3–3% | 0.75–2% |
| Flavoring agent | 0.05–5% | 0.1–2.5% | 0.1–2.5% |

It is particularly preferred to formulate the fill formulation for a 3 mg capsule:

|  | Amount |
|---|---|
| Polar solvent: |  |
| Polyethyleneglycol | 85% |
| Glycerine | 7.89% |
| Lecithin | 5.0% |
| Progesterone | 1.11% |
| Oil of Peppermint | 1.0% |

EXAMPLE 10
Fluoxetine Bite Capsule

A bite capsule of the invention comprises the following fill formulation:

|  | Amount | Preferred Amount | Most-Preferred Amount |
|---|---|---|---|
| Polar solvent | 75–99.8% | 75–99.8% | 85–99.5% |
| Emulsifier/wetting agents | 0–20% | 0–15% | 0–10% |
| Fluoxetine HCl | 0.2–9.25% | 0.4–6% | 0.75–4% |
| Flavoring agent | 0.05–5% | 0.1–2.5% | 0.5–3% |

It is particularly preferred to formulate the fill formulation for a 5 mg capsule:

|  | Amount |
| --- | --- |
| Polar solvent: | |
| Polyethyleneglycol | 85% |
| Glycerine | 7.15% |
| Lecithin | 5.0% |
| Fluoxetine HCl | 1.85% |
| Oil of Peppermint | 1.0% |

EXAMPLE 11

Piroxicam Bite Capsule

A bite capsule of the invention comprises the following fill formulation:

|  | Amount | Preferred Amount | Most-Preferred Amount |
| --- | --- | --- | --- |
| Polar solvent | 75–99.8% | 75–99.8% | 95–99.5% |
| Emulsifier/wetting agents | 0–20% | 0–15% | 0–10% |
| Piroxicam | 0.2–9.25% | 0.4–4% | 0.75–4% |
| Flavoring agent | 0.05–5% | 0.1–4.5% | 0.5–3% |

It is particularly preferred to formulate the fill formulation for a 5 mg capsule:

|  | Amount |
| --- | --- |
| Polar solvent: | |
| Polyethyleneglycol | 85% |
| Glycerine | 7.5% |
| Lecithin | 5.0% |
| Piroxicam | 1.85% |
| Oil of Peppermint | 1.0% |

EXAMPLE 12

Clemastine Fumarate with Phenylpropanolamine Hydrochloride Bite Capsule

A bite capsule of the invention comprises the following fill formulation:

|  | Amount | Preferred Amount | Most-Preferred Amount |
| --- | --- | --- | --- |
| Polar solvent | 40–99% | 50–98% | 70–98% |
| Emulsifier | 0–20% | 0–15% | 0–10% |
| Clemastine fumarate | 0.01–2% | 0.3–1.85% | 0.5–1.85% |
| Phenylpropanolamine HCl | 1–30% | 1.5–20% | 1.8–10% |
| Flavoring agent | 0.05–5% | 0.1–2.5% | 0.1–2.5% |

It is particularly preferred to formulate the composition fill for a clemastine 1.34 mg/25 mg phenylpropanolamine capsule:

|  | Amount |
| --- | --- |
| Polar solvent: | |
| Polyethyleneglycol | 78.73% |
| Water | 5.3% |
| Glycerine | 4.4% |
| Clemastine fumarate | 0.5% |
| Phenylpropanolamine HCl | 9.2% |
| Saccharine | 0.37% |
| Peppermint Oil | 1.5% |

EXAMPLE 13

Clemastine/Pseudoephedrine Bite Capsule

A bite capsule of the invention comprises the following fill formulation:

|  | Amount | Preferred Amount | Most-Preferred Amount |
| --- | --- | --- | --- |
| Polar solvent | 40–99% | 60–95% | 70–90% |
| Emulsifier | 0–20% | 0–15% | 0–10% |
| Clemastine fumarate | 0.01–2% | 0.3–1.85% | 0.5–1.85% |
| Pseudoephedrine HCl | 3–30% | 5–25% | 10–23% |
| Flavoring agent | 0.05–5% | 0.1–2.5% | 0.1–2.5% |

It is particularly preferred to formulate the composition fill for a 1.34 mg clemastine fumarate/60 mg pseudoephedrine HCl capsule:

|  | Amount |
| --- | --- |
| Polar solvent: | |
| Polyethyleneglycol | 65.71%% |
| Water | 5.30% |
| Glycerine | 4.40% |
| Clemastine fumarate | 0.50% |
| Pseudoephedrine HCl | 22.22% |
| Peppermint Oil | 1.5% |
| Saccharine | 0.37% |

What is claimed is:

1. A method of administering an effective amount of a pharmacologically active compound to a mammal in needed of same, by spraying the oral mucosa of said mammal with a buccal spray composition, formulated for dispensation from a pump spray means for transmucosal administration of said pharmacologically active compound dissolved in a pharmaceutically acceptable polar solvent, comprising in weight % of total composition: polar solvent 75–99.8%, active compound 0.68–40% wherein the active compound is selected from the group consisting of non-steroidal anti-inflammatories, anti-histamines, steroid hormones, benzodiazepams, and anti-depressants.

2. The method of claim 1 wherein the spray composition additionally comprising, by weight of total composition: flavoring agent 0.05–5%.

3. The method of claim 1 wherein the spray composition comprises polar solvent 75–99%, active compound 1–20%, flavoring agent 0.1–2.5%.

4. The method of claim 1 wherein the spray composition comprises polar solvent 75–98%, active compound 1–12.5%, flavoring agent 0.1–2.5%.

5. The method of claim 1, wherein the solvent is a selected from the group consisting of the alcohols of $C_{7-18}$ hydrocarbons of linear or branched configuration.

6. The method of claim 1 wherein the active compound is selected from the group consisting of clemastine, testosterone, estradiol, progesterone, temazepam, fluoxetine, and piroxicam in their nonionized form or as the pharmaceutically acceptable salts thereof.

7. The method of claim 1 wherein the flavoring agents are selected from the group consisting of synthetic or natural oil of peppermint, oil of spearmint, citrus oil, fruit flavors, sweeteners and combinations thereof.

8. The method of claim 2 comprising: polar solvent 75–99%, clemastine 0.12–10% and flavoring agent 0.05–5%.

9. The method of claim 1 wherein the amount of spray administered, is predetermined.

* * * * *

UNITED STATES PATENT AND TRADEMARK OFFICE
CERTIFICATE OF CORRECTION

PATENT NO.   : 6,110,486
DATED        : August 29, 2000
INVENTOR(S)  : Harry A. Dugger, III It is certified that error appears in the above-identified patent and that said Letters Patent is hereby corrected as shown below:

Column 10,
Line 55, replace "0.68-40%" with -- 0.68-20% --.

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,110,486 | Page 1 of 1 |
| APPLICATION NO. | : 09/199380 | |
| DATED | : August 29, 2000 | |
| INVENTOR(S) | : Harry A. Dugger, III | |

It is certified that error appears in the above-identified patent and that said Letters Patent is hereby corrected as shown below:

Column 10, line 47, cancel the text beginning with "1. A method of administering" and ending "diazepams, and anti-depressants." in line 58, and insert the following claim:

--1. A method of administering an effective amount of a pharmacologically active compound to a mammal in need of same, by spraying the oral mucosa of said mammal with a buccal spray composition, formulated for dispensation from a pump spray means for transmucosal administration of said pharmacologically active compound dissolved in a pharmacologically acceptable polar solvent, comprising in weight % of total composition: solar solvent 75-99.8%, active compound 0.68-40%, wherein the active compound is selected from the group consisting of non-steroidal anti-inflammatories, anti-histamines, steroid hormones, benzodiazepines, and anti-depressants.--

Signed and Sealed this

Seventeenth Day of August, 2010

David J. Kappos
*Director of the United States Patent and Trademark Office*